United States Patent [19]

Makin

[11] Patent Number: 4,474,994
[45] Date of Patent: Oct. 2, 1984

[54] PURIFICATION OF VANILLIN
[75] Inventor: Earle C. Makin, Dickinson, Tex.
[73] Assignee: Monsanto Company, St. Louis, Mo.
[21] Appl. No.: 417,314
[22] Filed: Sep. 13, 1982
[51] Int. Cl.³ ............................................. C07C 45/78
[52] U.S. Cl. ...................................... 568/438; 203/39
[58] Field of Search ......................... 568/438; 210/767
[56] References Cited
U.S. PATENT DOCUMENTS 3,477,856 11/1969 Schultz .................................. 99/105
4,075,248 2/1978 Marshall et al. ................ 568/438 X
4,198,432 4/1980 Vitzthum et al. ................... 426/312

FOREIGN PATENT DOCUMENTS 318939 9/1929 United Kingdom ................ 568/438

Primary Examiner—Bernard Helfin
Attorney, Agent, or Firm—Jon H. Beusen; James C. Logomasini; Arnold H. Cole

[57] ABSTRACT

Crude vanillin is purified by supercritical extraction of impurities. The process is especially useful in purifying crude vanillin obtained from paper mill waste liquors. Preferred supercritical extraction fluid is $CO_2$.

10 Claims, No Drawings

PURIFICATION OF VANILLIN

BACKGROUND OF THE INVENTION

1. Field of the Invention

The present invention relates to a process for the purification, by supercritical extraction, of crude vanillin, especially crude vanillin obtained from paper mill waste liquors.

2. Description of the Prior Art

Vanillin is the common name for 4-hydroxy-3-methoxybenzaldehyde.

Vanillin is the principal flavoring in vanilla, and for hundreds of years had been obtained by processing the seed pods of *vanilla planifolio* and *vanilla fragrans*. The seed pods were crushed and fermented and the vanillin extracted by alcohol.

Vanillin has also been prepared by processing parts of coniferous trees. Coniferon was extracted, then oxidized, and finally hydrolyzed to vanillin. See U.S. Pat. No. 151,119 (May 19, 1974), the teachings of which are incorporated herein by reference.

Vanillin has also been synthesized from eugenol, guaiacol, and safrole.

Most vanillin today is obtained from paper mill waste liquors. It was recognized as early as 1875 that the waste sulfite liquor contained some vanillin. The problem was concentration and purification of the crude vanillin in the paper mill waste liquors.

Commercially, vanillin is produced by the controlled oxidation of lignosulfonates, usually obtained from waste liquors.

A general scheme for the production of vanillin from waste sulfite cooking liquors involves adding the waste sulfite liquor, air, and NaOH to a reactor. This step is taught in U.S. pat. No. 2,692,291, the teachings of which are incorporated by reference.

The crude product, containing very dilute vanillin, may then be extracted with a solvent, e.g., 1-butanol, for removal of lignin salts. The somewhat purified vanillin solution is then subjected to bisulfite extraction by contacting the mixture of crude vanillin and 1-butanol with $NaHSO_3$ in a bisulfite extractor. The aqueous phase is then treated with $H_2SO_4$ and air in a blow tower to produce $SO_2$ and crude vanillin. The crude vanillin is then subjected to vacuum distillation, with the crude vanillin being recovered in the purified form overhead. Final purification is obtained by multiple crystallization. Such extensive and expensive purification steps are necessary because along with the vanillin are produced such compounds as acetovanillone, p-hydroxybenzaldehyde, 5-formyl vanillin, and syringic aldehyde. This general scheme for the production of vanillin is disclosed in Kirk-Othmer, *Encyclopedia of Chemical Technology*, 2nd. Edition, Volume 21, pp 180–196.

U.S. Pat. No. 3,049,566, the teachings of which are incorporated by reference, teaches purifying crude vanillin obtained via lignin oxidation by crystallization using a methanol-water solvent.

U.S. Pat. No. 3,600,442, the teachings of which are incorporated by reference, teaches treating the crystallization liquors with an alkali metal hydroxide and a zinc or magnesium salt to precipitate vanillin and acetovanillone. The vanillin is then separated from the acetovanillone by the bisulfite method.

A number of improvements have been suggested for extracting vanillin from the lignin liquor. U.S. Pat. No. 3,686,322, the teachings of which are incorporated by reference, teaches using a hot hydrocarbon solvent to extract the vanillin, then cooling the solvent to crystallize the vanillin.

The current processes for purifying crude vanillin are fairly successful, and perhaps inevitable, as far as concentrating the crude vanillin from the 1 to 15 weight percent range, as found in the waste liquor, and concentrating the vanillin. There is nonetheless a significant amount of energy expended in the final purification of vanillin, i.e., taking it from the 50 to 95 percent purity range to the 98–99+ percent purity range. The final purification step is very difficult because everything that is easy to remove from the crude vanillin, e.g., water, has already been removed in prior processing steps. The materials that remain with the vanillin have very similar chemical and physical properties such that conventional fractionation techniques are utterly inadequate, and only multistage crystallization has found favor in obtaining product of the desired high purity.

Some attempts have been made to bypass the problems of prior art methods. One early attempt involved the use of liquid $CO_2$ to extract flavors from natural spices. U.S. Pat. No. 3,477,856, the teachings of which are incorporated by reference, taught that liquid $CO_2$ could extract flavor essences from all kinds of materials which contain volatile flavoring components. Specific examples included spices such as pepper, cinnamon, bay, and also tea, coffee, cocoa, meats, and other materials of plant or animal origin. Liquid $CO_2$ was used as a solvent and the flavoring materials were recovered by vaporizing the liquid $CO_2$.

The use of $CO_2$ was taken one step further in U.S. Pat. No. 4,198,432, the teachings of which are incorporated by reference. The patentee found that it was possible to extract flavor and aroma constituents from natural spices selected from the group of black pepper, cloves, cinnamon, and vanilla by dry supercritical extraction followed by wet supercritical extraction. The dry supercritical extraction dissolved the aroma constituents from the spice, while the wet supercritical extraction dissolved the flavor constituents of the natural spices.

Unfortunately, the problems encountered in extracting flavor and aroma components from natural spices are quite different than those encountered in extracting vanillin from aqueous streams. For one thing, many of the flavor and aroma constituents in natural spices are not water soluble, whereas the vanillin in spent sulfite liquors is in water solution. None of the prior art methods of purifying vanillin obtained from spent cooking liquors were completely satisfactory as they required a lot of energy and effort to recover vanillin, at great purity, from a relatively dilute solution. The use of $CO_2$, either as a liquid or supercritical fluid, for processing of natural spices did not provide much guidance because the starting materials were different, and these methods taught extracting small amounts of flavor and aroma components from large amounts of vegetable matter. All of these prior art methods missed the target because they focused on recovering the vanillin rather than removing the impurities.

I have discovered an economical and effective way of purifying crude vanillin derived from lignin and similar materials. My method is economical because it extracts the impurities, leaving as a valuable residue purified vanillin.

SUMMARY OF INVENTION

Accordingly, the present invention provides a process for the purification of crude vanillin contaminated with impurities comprising contacting the crude vanillin with a supercritical extraction fluid at supercritical extraction conditions, extracting from the crude vanillin at least some of the impurities, and separating the supercritical fluid containing impurities from the crude vanillin to produce vanillin product with increased purity.

In a more limited embodiment, the present invention provides a process for purifying crude vanillin obtained from spent sulfite liquors, containing 70 to 98 weight percent vanillin, comprising contacting said crude vanillin at a temperature of 35 to 50 C. and pressures of 40 to 100 atmospheres with $CO_2$ whereby the $CO_2$ extracts impurities from the crude vanillin to produce a purified vanillin product.

DETAILED DESCRIPTION

The crude vanillin which is purified by the process of my invention can be obtained from any source except vanilla beans. Vanillin from coniferon, eugenol, guaiacol, safrole, or preferably vanillin from wood products, e.g., lignins, lignosulfonates, or spent sulfite cooking liquor, is a suitable feedstock.

The crude vanillin should have a vanillin concentration of at least 50 weight percent. Preferably the crude vanillin has a concentration in excess of 70-85 weight percent, with vanillin contents of around 90 to 98 weight percent being ideal for the practice of my invention. Although it may be possible to apply the process of my invention to somewhat more dilute vanillin streams than hereinbeforementioned, it is not efficient or economical to do so because the amount of impurities extracted tend to overwhelm my process. Phrased more simply, my process works best when the crude vanillin has been substantially concentrated and purified by conventional means. My process is very efficient and economical for obtaining a very pure final product, but is not especially economical for, e.g., removing water or inorganics present in large amounts, such as calcium sulfite.

The supercritical extraction process can be performed in any convenient and acceptable manner, either batch or continuous. In a batch process the crude vanillin and supercritical fluid can simply be added to a batch reactor, preferably one equipped with stirring means, and allowed to come to equilibrium. The fluids in the batch reactor could be separated by simply gravity settling and the materials separately withdrawn to effect separation of contaminants from vanillin. In one aspect of a continuous mode of operation for illustrative purposes, melted crude vanillin is sprayed into the extractor under pressure whereupon the minute droplets solidify and fall countercurrent to the extraction fluid.

The pressure, temperature, and residence time within the supercritical extraction zone can be determined by experimentation based upon the desired product purity, the amount and nature of impurities present in the vanillin, and the supercritical extraction fluid.

Any supercritical extraction fluid which has a preference for the impurities commonly found in crude vanillin streams can be used. Especially good fluids are $CO_2$, ethane, and ethylene. $CO_2$ is the ideal fluid.

Other fluids which may work include propane, unsaturated hydrocarbons containing up to 3 carbon atoms, nitrous oxide, sulfur hexafluoride, and mixtures of these materials with the aforementioned preferred fluids.

I was not able to note any difference between wet supercritical fluids and dry supercritical fluids, although such a distinction was made in U.S. Pat. No. 4,198,432. I know that liquid $CO_2$ does not work at all in the preactice of my invention, while supercritical $CO_2$ works very well, as will be shown by the Examples presented later on in this specification.

When operating the $CO_2$ on a crude vanillin of about 90–95 percent purity, temperatures between 31.6 and about 90 C., preferably 32 to 50 C., and pressures of 25 to 500 atmospheres, absolute, preferably 40 to 400 atmospheres, with very good results being obtained at 40 to 100 atmospheres, are used. Depending upon the efficiency of the contact of the crude vanillin with the $CO_2$, contact times of the crude vanillin and $CO_2$ can range from 0.01 to 1,000 minutes, preferably 1 to 100 minutes.

Lower temperatures are preferred because they do not decompose or degrade the vanillin as much as high temperatures. Higher temperatures give greater product purity, but at a cost of somewhat reduced recovery, due to more extraction of vanillin at high temperatures.

The ratio of supercritical fluid to crude vanillin depends on the supercritical fluid, the extraction conditions, the amount and nature of contaminants, and desired product purity. When using $CO_2$, the weight ratio of $CO_2$:crude vanillin may range from 1:1 to 100:1, and preferably is 10:1 to 30:1. On a volume basis, the ratio of crude vanillin:supercritical extraction fluid, as measured at supercritical extraction conditions may range from 1:1 to 1:100, perferably 10:1 to 30:1.

EXAMPLE I

Into a small Soxhlet extractor contained in a high pressure autoclave were placed 10 g of a crude vanillin extracted from hydrolyzed paper mill waste. The crude vanillin contained.

| COMPONENT | WT. % |
| --- | --- |
| Guaiacol | 3.14 |
| Vanillin | 82.20 |
| Acetovanillone | 9.39 |
| Light Ends & Tars | 5.27 |
| | 100.00 |

The autoclave was heated to 40 C. for one hour. To autoclave contained 150 g $CO_2$. The autoclave pressure was 53 atmospheres, absolute. The supercritical gas extracted out 24.6 percent of the feed (2.46 grams) leaving an unextracted residue (7.54 grams) of the following composition:

| COMPONENT | WT. % |
| --- | --- |
| Guaiacol | 0.84 |
| Vanillin | 92.92 |
| Acetovanillone | 5.15 |
| Light Ends & Tars | 1.19 |
| | 100.10 |

Over 85 percent of the vanillin is recovered at a greatly improved quality.

EXAMPLE II

Example I was repeated using an extraction temperature of 35 C. After one hour extraction purified vanillin residue consisting of 8.14 g of product with a vanillin purity of 91.7 weight percent was recovered. The purified vanillin recovered represented 90.8 percent of the vanillin placed in the extractor.

EXAMPLE III

Example I was repeated using an extractor temperature of 45 C for one hour. Purified vanillin was recovered at 92.51 percent purity and represented 76.2 percent of vanillin in the crude feed to the autoclave.

EXAMPLE IV (Calculated Operation)

Impurities are removed from crude vanillin at 50–60 percent per stage based on the autoclave tests cited in preceding Examples. Two calculated cases summarized below show the capability of a multistage countercurrent flow extractor using supercritical $CO_2$ as the solvent.

| Case | I | II |
|---|---|---|
| Wt. % Vanillin in Feed | 82.2 | 82.2 |
| % Removal of Impurities per Stage (Assumption) | 50 | 60 |
| Vanillin recovery, per Stage %, (Assumption) | 91 | 88 |
| Temperature, °C. | 35 | 35 |
| Pressure, atm | 53 | 53 |
| Number of Stages | 5 | 5 |
| Vanillin Purity at Stage | | |
| 1 | 91.1 | 92.7 |
| 2 | 95.6 | 97.1 |
| 3 | 97.8 | 98.8 |
| 4 | 98.9 | 99.5 |
| Wt. % Vanillin in Purified Product | 99.4 | 99.8 |
| Overall Vanillin Recovery, % | 62.4 | 52.8 |

EXAMPLE V (Prior Art—Liquid $CO_2$)

I repeated the experiments I–III at 25 C., which gave liquid $CO_2$ instead of supercritical $CO_2$. The liquid $CO_2$ had absolutely no effect on the crude vanillin. Nothing dissolved. I rechecked this experiment by letting it continue for four hours, but the liquid $CO_2$ still did nothing.

The vanillin product obtained by my process is suitable for use as a food chemical, pharmaceutical intermediate, or for use in perfumes, odor fixatives, etc.

Using the process of my invention, it should be possible to purify crude vanillin streams commercially for a fraction of the cost per pound of conventional distillation and crystallization techniques. The prior art methods of vanillin production, e.g., vacuum distillation followed by multiple crystallization, are costly due to energy requirements and degradation of vanillin in the processing steps resulting in significant yield losses, so my method results in a significant cost savings.

Further economies may be realized by modifying the current vanillin production process to take advantage of the efficiency of my vanillin purification process. These modifications may be, e.g., less reflux on a column to give a crude vanillin of less purity, and at much less energy cost. The final purification and concentration of crude vanillin can be economically achieved using my process to polish the contaminated vanillin to a higher purity product.

World consumption of vanillin for 1970 was estimated at 8.8 million pounds, and I believe that there is a substantially higher consumption now. The practice of the present invention should result in reduced costs of manufacturing this important and valuable commodity.

The term, supercritical extraction conditions, as used in the specification and claims, includes a temperature above the critical temperature of the extraction fluid, but does not have to include a supercritical pressure. In fact, my work with supercritical $CO_2$ was always below the critical pressure of $CO_2$, but above the critical temperature.

I claim:

1. A process for purification of crude vanillin, comprising:

a. contacting crude vanillin obtained from lignin, lignosulfonates, or sulfite cooking liquor comprising at least 50 weight percent vanillin with a supercritical extraction fluid which preferentially dissolves the impurities in the crude vanillin, selected from the group consisting of $CO_2$, ethane, and ethylene, at a temperature in excess of the critical temperature of the extraction fluid and at a pressure of 25 to 500 atmospheres;

b. extracting from the crude vanillin at least some of the impurities; and c. separating the supercritical fluid containing impurities from the crude vanillin to produce vanillin product with increased purity.

2. Process of claim 1 wherein the crude vanillin comprises 70 weight percent vanillin.

3. Process of claim 1 wherein the impurities in the crude vanillin include one or more of acetovanillone, p-hydroxybenzaldehyde, 5-formyl vanillin, syringic aldehyde, and mixtures thereof.

4. Process of claim 1 wherein the supercritical extraction fluid is $CO_2$.

5. Process of claim 4 wherein the supercritical extraction conditions include a temperature of 31.6 to 90 C. and a pressure of 25 to 500 atmospheres, absolute.

6. Process of claim 4 wherein supercritical extraction conditions include a temperature of 35 to 50 C. and a pressure of 40 to 100 atmospheres, absolute.

7. Process of claim 4 wherein the volume ratio of $CO_2$ to crude vanillin is 1:1 to 100:1, on a volumetric basis as measured at supercritical extraction conditions.

8. Process of claim 4 wherein the weight ratio of $CO_2$ to crude vanillin is 10:1 to 30:1.

9. Process of claim 1 wherein the residence time of crude vanillin within the supercritical extraction zone is 1 to 1,000 minutes.

10. A process for purifying crude vanillin, obtained from spent sulfite liquors containing 70 to 98 weight percent vanillin, comprising contacting said crude vanillin at a temperature of 35 to 50 C., and pressure of 40 to 100 atmospheres with $CO_2$, whereby the $CO_2$ extracts impurities from the crude vanillin, to produce a purified vanillin product.

* * * * *